United States Patent [19]

DeMoreta

[11] Patent Number: 5,083,317

[45] Date of Patent: Jan. 28, 1992

[54] SUN SCREEN HAT

[76] Inventor: Daniel F. DeMoreta, 72 St. Clair Avenue, St. Clair, NSW, Australia

[21] Appl. No.: 507,977

[22] Filed: Apr. 11, 1990

[51] Int. Cl.⁵ .............................................. A42B 1/00
[52] U.S. Cl. ............................................. 2/174; 2/12; 2/177; 2/198
[58] Field of Search ..................... 2/12, 15, 171, 172, 2/174, 177, 184.5, 198, 209.3, 175, 200

[56] References Cited

U.S. PATENT DOCUMENTS

| | | | |
|---|---|---|---|
| 986,728 | 3/1911 | Lee | 2/174 |
| 2,005,361 | 6/1935 | Rollins | 2/198 |
| 2,296,078 | 9/1942 | Young | 2/174 |
| 2,424,744 | 7/1947 | Dicken | 2/174 |
| 2,629,869 | 3/1953 | Locken | 2/174 |
| 2,663,024 | 12/1953 | Cantor | 2/177 |
| 2,767,404 | 10/1956 | Collins | 2/198 |
| 2,791,778 | 5/1957 | Wardley | 2/174 |
| 2,897,510 | 8/1959 | Robinson | 2/198 |
| 3,235,882 | 2/1966 | Coleman | 2/174 |
| 4,771,477 | 9/1988 | Cahill | 2/12 |

*Primary Examiner*—Werner H. Schroeder
*Assistant Examiner*—Diana L. Biefeld
*Attorney, Agent, or Firm*—Lackenbach Siegel Marzulio & Aronson

[57] ABSTRACT

A sun screen hat formed from a planar sheet of flexible, slightly stretchable, pliant, sunblocking material. The hat has generally a brim section, an adjoining and extending skirt section and a generally circular opening at least partly within the brim section to define a rim band. The pliant hat material is self-draping so that when the hat is worn, the skirt section hangs down in vertical folds at the back of the wearer's head and neck, and if desired, parts of the shoulders, and folds into a hanging drape-like shape.

14 Claims, 1 Drawing Sheet

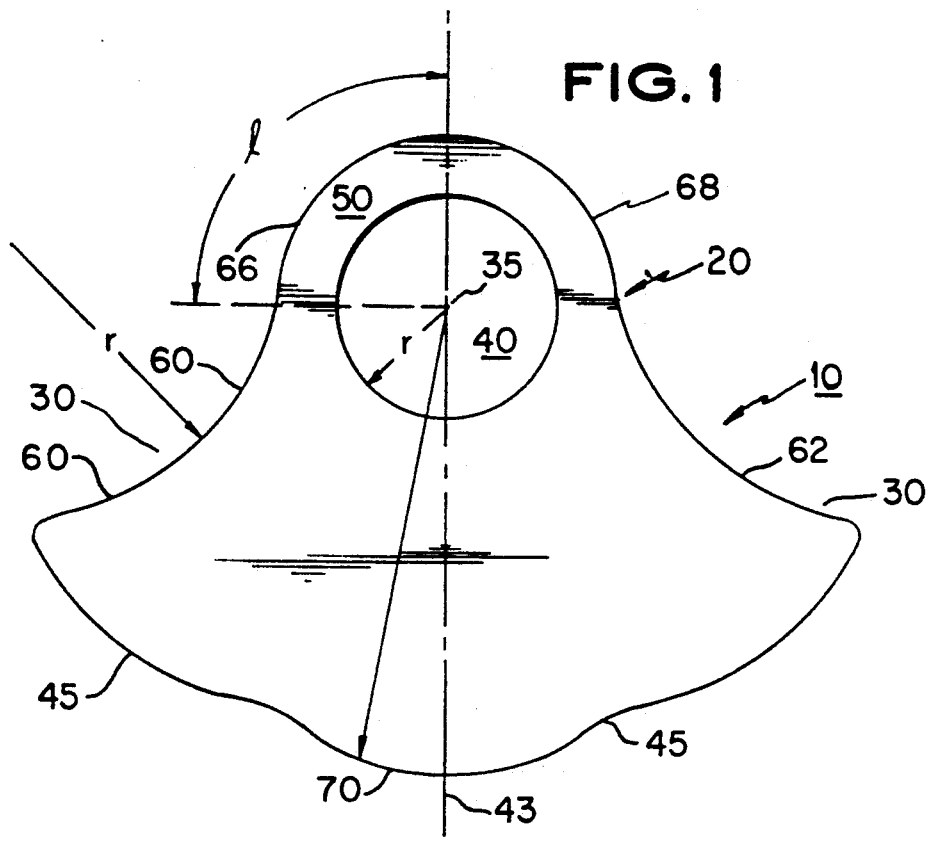
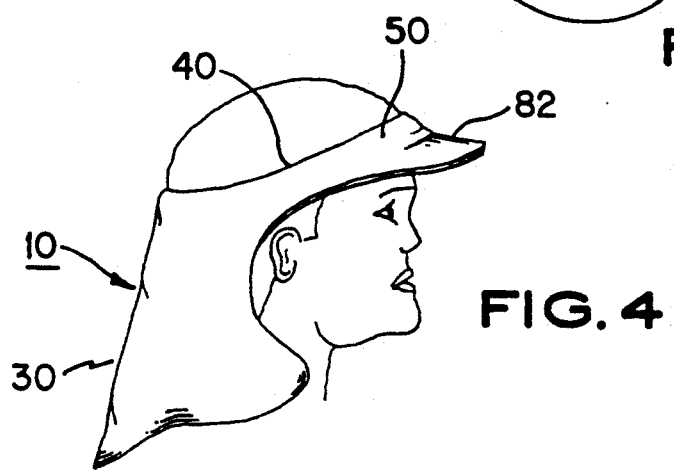

SUN SCREEN HAT

FIELD OF THE INVENTION

The invention relates to a hat for providing protection against sunlight to the wearer's neck. More particularly, the invention relates to a crownless hat formed from a flexible, planar material which is configured for easy wear and storage.

BACKGROUND OF THE INVENTION

Sunblocking headwear for protecting the wearer's neck and shoulders are widely used and mostly involve rigid or semi-rigid rims and visors, or multi-element structures with various non-planar geometric configurations.

SUMMARY OF THE INVENTION

A hat in accordance with the present invention is formed from a relatively thin, planar, pliant, at least slightly stretchable, self-draping material. That is, the hat material is capable of laying flat without significant application of external force, and the same is true of the hat formed therefrom. When placed over an object, the above-noted hat material will hang to fit the covered object in loose lines, and drape itself in loose folds, and rest limply on the object. Suitable materials for the hat of the present invention are elastomeric materials, such as neoprene sheet, which can be laminated, if desired, and sheets or mats of polymeric material, e.g. synthetic foams, such as polyethylene foam. These materials should be selected to be substantially opaque to sunlight. The thickness of the material can suitably range from about 0.02 inch to 0.5 inch, so long as the material retains the above-mentioned pliant and self-draping properties. Thicknesses outside of the above-mentioned range are likewise suitable if the noted properties are retained by the material.

The planar hat material is shaped to have a generally semicircular brim section and a contiguous, adjoining skirt section which has opposed lateral edge portions, each of which extends outwardly from the brim section, and from each other. The lateral edge portions are joined by an end edge portion. A generally circular head opening is provided in the hat material and the material is at least slightly stretchable to permit the wearer's head to comfortably fit and engage the head opening in the material.

In a selected embodiment, the skirt section is fan-shaped and tangentially joins a generally semicircular brim section to provide a generally bell-shaped symmetrical configuration with a relatively narrow semicircular rim band defined by the head opening and the brim section of the hat.

In a further and preferred embodiment, the generally semicircular brim section extends away from the skirt section and the head opening by a distance sufficient to shade the eyes of the wearer.

BRIEF DESCRIPTION OF THE DRAWINGS

FIG. 1 shows a top plan view of a planar hat in accordance with the present invention;

FIG. 2 shows a perspective view of the hat of FIG. 1;

FIG. 3 shows a further embodiment of the present invention having an extended brim portion and completely bounded by curvilinear edges; and FIG. 4 shows a hat in accordance with a preferred embodiment of the present invention being worn and protecting the neck of the wearer and providing an extended brim portion to protect the eyes of the wearer.

DETAILED DESCRIPTION OF THE INVENTION

With reference to the drawing which illustrates a preferred embodiment of the present invention, FIG. 1 shows, at 10, a planar material, of relatively thin and uniform width (shown at 15 in FIG. 2), which is flexible, pliant and at least slightly stretchable. The hat material 10 is configured to have a brim section 20, shown in FIG. 1 to be semi-circular in shape, and a contiguous skirt section 30, shown in FIG. 1 to be fan-shaped. The overall configuration of the hat of FIG. 1 is generally bell-shaped and symmetrical about an axis through the center 35 of a generally circular opening 40, and the midpoint 43 of end edge 45 of skirt section 30. Opening 40 is located partly in the brim section 20 and is shown, in FIG. 1, suitably concentric with semi- circular brim section 20 and defines therewith a relatively narrow, semicircular rim band 50. The lateral, i.e. side edges 60, 62 of skirt section 30, are tangential to the respective side edges 66, 68 of the brim section 30, and, in the embodiment of FIG. 1, flare outwardly from the brim section 30 and from each other. In FIG. 1, the outwardly extending lateral edges 60, 62 of skirt section 30 are circular arc lengths having a radius "r", which is larger than the radius "r" of the semi-circular brim section 20. The arc length of each side edge 60, 62 is preferably 1½ to 2 times the length "l" of one-half the semicircular brim section 20. The end edge 45 of skirt section 30 is arcuate in shape and extends away from the brim section 30 and, as shown in FIG. 1, has a protruding portion 70 which is in the shape of a circular arc length which is concentric with semicircular brim section 20.

FIG. 3 shows a hat in accordance with the present invention having an extended brim section 80 which results in the formation of an eye-shading brim or a small visor, shown at 82 in FIG. 4. The hat of FIG. 3 is completely curvilinear in shape with arcuate edges on all sides. The extended brim section 80 can be provided by locating and sizing the head opening 40 so that, with reference to FIG. 3, the width, $W_1$ of the visor-like extension 80, is greater than the width, $W_2$, of the adjoining lateral side portions 83, of brim section 20 (e.g. from about 1.1 to 3 times greater); and FIG. 4 shows a hat of the type described above in connection with FIGS. 1 and 3 on the head of a wearer and draped over the back of the wearer's head in loose folds and shielding the wearer's neck.

As can be seen from the foregoing description, the hat of the present invention can be easily made and worn and provides protection against strong sunlight at the neck of the wearer. When not in use, the hat can be easily stored.

While the present invention has been described with particularity, it will be understood that the details may be varied through a wide range without departing from the principles of this invention.

What is claimed is:

1. A hat formed from a unitary single piece of material from relatively thin, planar, flexible, pliant, at least slightly stretchable, self-draping material comprising
   a continuous and nonreparable brim section;
   a single nonreparable skirt section contiguously adjoining said brim section and being continuous with and non-separable from said brim section having opposed lateral edge portions joined by an end edge portion, said opposed lateral edge portions of said skirt section extending outwardly from said adjoining brim section and away from each other, said hat having a generally circular opening at least partly within the continuous brim section and partly within the skirt section.

2. A hat in accordance with claim 1 wherein said brim section is substantially semicircular in shape.

3. A hat in accordance with claim 2 wherein said semicircular brim section and said generally circular opening in the hat define therebetween a relatively narrow semicircular rim band.

4. A hat in accordance with claim 1 wherein said skirt section is fan-shaped and the opposed lateral edge portions of the skirt section flare outwardly from the brim section and from each other.

5. A hat in accordance with claim 4 wherein the opposed lateral edge portions are each in the form of arcs having a length from about 1¼ to 2 times greater than one-half that of the semicircular brim section.

6. A hat in accordance with claim 1 wherein the opposed lateral edge portions of said skirt section extend, respectively, tangentially from said brim portion.

7. A hat in accordance with claim 1 wherein the opposed lateral edge portions of said skirt section extend, respectively, tangentially from said brim portion, said opposed lateral edge portions being in the form of circular arcs having a radius which is greater than the radius of the semicircular brim portion.

8. A hat in accordance with claim 1 wherein the opposed lateral edge portions of said skirt section extend, respectively, tangentially from said brim portion, said opposed lateral edge portions being in the form of circular arcs having a radius which is greater than the radius of the semicircular brim portion, each of said arcs having a length greater than one-half that of the semicircular brim section.

9. A hat in accordance with claim 1 wherein the end edge portion of the skirt section is arcuate and extends in a direction away from the rim section.

10. A hat in accordance with claim 1 wherein the end edge portion of the skirt section is arcuate and extends in a direction away from the rim section and has a protruding central portion which is substantially concentric with said semicircular brim section.

11. A hat in accordance with claim 1 wherein said planar material is substantially bell-shaped and symmetrical about an axis passing through the center of a circle defining the semicircular brim section and through the midpoint of the end edge portion of the skirt section.

12. A hat in accordance with claim 1 consisting solely of a unitary planar sheet of material of constant thickness, the brim section and skirt section being integral with said sheet.

13. A hat in accordance with claim 1, wherein said brim section and said generally circular opening in the hat define therebetween a rim band, said rim band having a width at the portion thereof most remote from the skirt section which is greater than the width of the adjoining side portions of the rim band.

14. A hat formed from relatively thin, planar, flexible, pliant, at least slightly stretchable, self-draping material comprising a semicircular brim section;

a skirt section contiguously adjoining said brim section having opposed lateral edge portions joined by an end edge portion, wherein the end edge portion of the skirt section is arcuate and extends in a direction away from the brim section and has a protruding central portion which is substantially concentric with said semicircular brim section, said opposed lateral edge portions of said skirt section extending outwardly from said adjoining brim section and away from each other, said hat having a generally circular opening at least partly within the brim section and consisting solely of a unitary planar sheet of material of constant thickness, the brim section and skirt section being integral with said sheet.

* * * * *